United States Patent [19]

Cincotta et al.

[11] 4,255,578

[45] Mar. 10, 1981

[54] SYNTHESIS OF PERHALOMETHYLCARBINOL-SUBSTITUTED PHENOL AND NAPHTHOL SULFAMPHTHALEIN DYES FROM THE CORRESPONDING TRIACYLATED DERIVATIVES

[75] Inventors: Louis Cincotta; James W. Foley, both of Andover, Mass.

[73] Assignee: Polaroid Corporation, Cambridge, Mass.

[21] Appl. No.: 956,907

[22] Filed: Nov. 2, 1978

[51] Int. Cl.³ .............................................. C07D 275/04
[52] U.S. Cl. ........................................ 546/96; 544/62; 546/198; 548/207; 548/210; 544/133; 544/135
[58] Field of Search ................... 544/33, 62, 133, 135, 544/368, 98; 546/95, 96, 198; 260/239 R, 301, 304; 548/207, 210

[56] References Cited

PUBLICATIONS

Abramovitch, R., J. Chem. Soc., Perkin Trans. I, 1974 (22) p. 2589.
Mustafa, A., J. Chem. Soc., (1952), p. 1339.
Dutt, J. Chem. Soc., 121, p. 2389 (1922).
Beilstein "Handbuch der Organischen Chemie", vol. 27, p. 534.
Bartlett, R. et al., J. Chem. Soc., 1939, 760–762.
Morrison, R. et al., "Organic Chemistry", 3rd ed., Allyn & Bacon, Inc., Boston, 1974, pp. 677 & 794.
Ber. 29 p. 1049 (1896).

*Primary Examiner*—Nicholas S. Rizzo
*Attorney, Agent, or Firm*—Sybil A. Campbell

[57] ABSTRACT

The present invention is concerned with a method of synthesizing certain

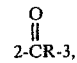

3-disubstituted sulfam(na)phthalein compounds useful as pH-sensitive indicator dyes and with intermediates useful in the preparation of said compounds. The subject method comprises (1) reacting (a) a 3,3-disubstituted sulfam(na)phthalein wherein one of the 3-substituents is a 4′-hydroxy-1′-phenyl moiety or a 4′-hydroxy-1′-naphthyl moiety substituted in the 3′-position with a perhalomethylcarbinol group and (b) an acid halide,

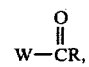

wherein R is alkyl or aryl to give (c) an acylated intermediate wherein the N atom of the sulfam(na)phthalein ring and the 4′-hydroxy and carbinol hydroxy groups are acylated with

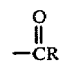

and (2) treating said compound (c) with alkali to selectively remove said

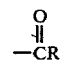

from said hydroxy groups and yield the

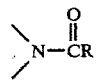

product. The intermediates of the present invention are the acylated compounds (c).

39 Claims, No Drawings

SYNTHESIS OF PERHALOMETHYLCARBINOL-SUBSTITUTED PHENOL AND NAPHTHOL SULFAMPHTHALEIN DYES FROM THE CORRESPONDING TRIACYLATED DERIVATIVES

BACKGROUND OF THE INVENTION

1. Field of the Invention

This invention relates to the preparation of certain N-acylated sulfam(na)phthaleins derived from phenols and 1-naphthols, to intermediates useful in the preparation thereof and to the preparation of said intermediates.

2. Description of the Prior Art

Various procedures have been reported for synthesizing 3-substituted-benz[d]isothiazole-1,1-dioxides and 3,3-disubstituted-2,3-dihydrobenz[d]isothiazole-1,1-dioxides from saccharin (3-oxo-2,3-dihydrobenz[d]isothiazole-1,1-dioxide) and from saccharin pseudo-chloride (3-chlorobenz[d]isothiazole-1,1-dioxide). As reported by A. Mustafa et al, J. Chem. Soc., 1952, p. 1339, the treatment of saccharin pseudo-chloride with excess phenylmagnesium bromide gave the corresponding 3,3-diphenyl-2,3-dihydrobenz[d]isothiazole-1,1-dioxide in almost quantitative yield. Methyl-, ethyl-, n-propyl- and n-butylmagnesium halides were reported by these authors to react analogously. R. A. Abramovitch et al, J. Chem. Soc., Perkin Trans I, 1974 (22), p. 2589, reviewed and reinvestigated the reactions of saccharins with alkyl and aryl Grignard reagents and found that either the 3-alkyl (or 3-aryl)-benz[d]-isothiazole-1,1-dioxide and/or the open-chain tertiary alcohol, o—CH$_2$OH benzenesulfonamide wherein R is alkyl (or aryl) were obtained with one exception. When saccharin was treated with an excess of phenylmagnesium bromide in boiling tetrahydrofuran, 3,3-diphenyl-2,3-dihyrobenz[d]isothiazole-1,1-dioxide was obtained as the minor product together with the open-chain tertiary alcohol.

R. A. Abramovitch et al also investigated the reaction of saccharin and saccharin pseudo-chloride with organolithium compounds and found that the reaction of saccharin with alkyl- and aryllithium compounds, such as, n-butyllithium and p-methoxyphenyllithium in tetrahydrofuran at −78° C. gave the corresponding 3-substituted-benz[d]-isothiazole-1,1-dioxide, exclusively. In addition to this general method for synthesizing 3-alkyl (or 3-aryl)-benz[d]-isothiazole-1,1-dioxides, the authors reported that the reaction of the pseudo-chloride with organolithium compounds, such as, n-butyllithium in tetrahydrofuran at −78° C. gave the corresponding 3,3-disubstituted-2,3-dihydrobenz[d]-isothiazole-1,1-dioxide as the major product.

Besides the reactions with Grignard and organolithium reagents, Friedel-Crafts reactions with the saccharins also have been disclosed. Dutt, J. Chem. Soc., 121, p. 2389 (1922) reported that condensation of saccharin with aromatic amines and phenols in the presence of concentrated sulfuric acid and also in the presence of fused zinc chloride. The resulting condensation products with saccharin were named "sulfamphthaleins" by analogy to "phthaleins" and "sulfonephthaleins". Though the structure of 3,3-di(4'-hydroxyphenyl)-2,3-dihydrobenz[d]isothiazole-1,1-dioxide (named "phenolsulfamphthalein") was assigned to the condensation product obtained with saccharin and phenol, it has been determined that the compound corresponding to the proposed structure has properties different from those reported, for example, colorless rather than pink in alkali and also, that the compound corresponding to the structure given could not be synthesized by repeating the procedures reported by Dutt.

Copending U.S. patent application Ser. No. 836,010 of Stanley M. Bloom, Alan L. Borror and James W. Foley filed Sept. 23, 1977 is directed to a method of synthesizing phenol and 1-naphthol sulfamphthaleins and sulfamnaphthaleins possessing a carbonyl group in the 2-position of the sulfam(na)phthalein ring. As disclosed and claimed therein, the method of preparing these compounds comprises reacting a 3-(4'-OP-1'-phenyl/4'-OP-1'-naphthyl)-3-(phenyl/naphthyl)-sulfam(na)phthalein wherein P is a protecting group with a carboxylic acid halide to yield the corresponding 2-carbonyl derivative followed by removing the protecting group with weak acid to yield the product.

The 3-(4'-OP-1'-phenyl/4'-OP-1'-naphthyl)-3-(phenyl/naphthyl)-2,3-dihydrobenz[d]isothiazole-1,1-dioxides employed as starting materials in the above method may be synthesized by reacting a 3-(4'-OP-1'-phenyl/4'-OP-1'-naphthyl)benz[d]-isothiazole-1,1-dioxide and a phenyllithium or a naphthyllithium reagent as disclosed and claimed in copending U.S. patent application Ser. No. 836,008 of Alan L. Borror, Louis Cincotta, James W. Foley and Marcis M. Kampe filed Sept. 23, 1977. As discussed therein, the 3-(4'-OP-1'-phenyl/4'-OP-1'-naphthyl)benz[d]isothiazole-1,1-dioxides are prepared by blocking the functional hydroxy group and any substituent group(s), as may be appropriate, of the selected 4-halophenol or 4-halo-1-naphthol and converting the blocked phenol or 1-naphthol to the corresponding Grignard or lithium reagent which is then reacted with a saccharin reagent. The phenyl- or naphthyllithium reagent reacted with the 3-(4'-OP-1'-phenyl/4'-OP-1'-naphthyl)benz[d]isothiazole-1,1-dioxide may be substituted or unsubstituted and may be prepared from the corresponding halo-substituted compound by reacting with lithium metal or n-butyllithium to yield the lithium reagent. If substituents, such as, hydroxy, are present, they are blocked with the appropriate protecting group to render them compatible with organometallic reagents prior to conversion to the lithium compound. The protecting groups selected should be removable under mildly acidic conditions so that the blocked substituents can be regenerated simultaneously with the regeneration of the functional —OH group of the 4'-OP-1'-phenyl or 4'-OP-1'-naphthyl moiety. Starting materials for use in the method of aforementioned application Ser. No. 836,010 also may be prepared according to the method of copending U.S. patent application Ser. No. 836,025 of Alan L. Borror, James W. Foley, Marcis M. Kampe and John W. Lee, Jr. filed Sept. 23, 1977, now U.S. Pat. No. 4,178,447, which comprises reacting a 3-(phenyl/naphthyl)benz[d]isothiazole-1,1-dioxide and a 4'-OP-phenyl/4'-OP-naphthyllithium compound to give the corresponding 3-(phenyl/naphthyl)-3-(4'-OP-1'-phenyl/4'-OP-1'-naphthyl)-2,3-dihydrobenz[d]isothiazole-1,1-dioxide wherein P represents a protecting group compatible with organometallic reagents which is capable of being removed in weak acid to regenerate the free —OH.

The present invention is concerned with a method of preparing perhalomethylcarbinol-substituted phenol and 1-naphthol sulfamphthaleins and sulfamnaphthaleins possessing a certain 2-carbonyl substituent on the sulfam(na)phthalein ring wherein the blocking of the phenolic (or naphtholic) hydroxy group and the carbinol hydroxy group of the 4'-hydroxy-3'-perhalomethylcarbinol-1'-phenyl/naphthyl moiety of the starting sulfam(na)phthalein with a protecting group, P, is eliminated.

SUMMARY OF THE INVENTION

It is, therefore, one object of the present invention to provide a novel method of synthesizing certain 2-acylated sulfam(na)phthaleins derived from perhalomethylcarbinol-substituted phenols and 1-naphthols.

It is another object of the present invention to provide novel intermediates useful in the synthesis of said 2-acylated sulfam(na)phthaleins.

Other objects of this invention will in part be obvious and will in part appear hereinafter.

This invention accordingly comprises the process involving the several steps and the relation and order of one of more of such steps with respect to each of the others and the product possessing the features, properties and the relation of elements which are exemplified in the following detailed disclosure and the scope of the application of which will be indicated in the claims.

According to the present invention, it has been found quite unexpectedly that when a certain class of acyl halides is reacted with a 3-(4'-hydroxy-3'-perhalomethylcarbinol-1'-phenyl/4'-hydroxy-3'-perhalomethylcarbinol-1'-naphthyl)-3-(phenyl/naphthyl)-2,3-dihydrobenz[d]isothiazole-1,1-dioxide (or -2,3-dihydronaphtho[1,8-de]-1,2-thiazine-1,1-dioxide), the acyl groups may be removed from the 4'-hydroxy and carbinol hydroxy groups of the acylated compound obtained without removing the acyl group from the N atom, i.e., the 2-position of the isothiazole or 1,2-thiazine ring. Because the acyl groups may be selectively removed from the said hydroxy groups while leaving the N-acyl group on the isothiazole or 1,2-thiazine ring, the 4'-hydroxy and carbinol hydroxy groups of the 3,3-disubstituted compounds reacted with the acyl halide need not be blocked with a protecting group prior to the acylation reaction.

For a fuller understanding of the nature and objects of the present invention, reference should be had to the following detailed description.

DETAILED DESCRIPTION OF THE INVENTION

Specifically, the method of the present invention comprises (1) reacting (a) a compound of the formula

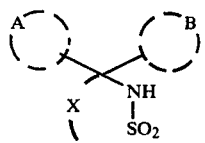

wherein A is selected from a 4'-hydroxy-1'-naphthyl moiety substituted in the 3'-position with a group,

wherein $R^I$ is perhalomethyl and $R^{II}$ is hydrogen or perhalomethyl and a 4'-hydroxy-1'-phenyl moiety substituted in the 3'-position with a group,

wherein $R^I$ is perhalomethyl and $R^{II}$ is hydrogen or perhalomethyl; B is a phenyl moiety or a naphthyl moiety provided B is a phenyl moiety when said A is said 4'-hydroxy-1'-naphthyl moiety and X represents the atoms necessary to complete a ring-closing moiety selected from a sulfamphthalein moiety and a sulfamnaphthalein moiety and (b) an acid halide of the formula $$W-\overset{O}{\underset{\|}{C}}R$$

wherein W is chloro or bromo and R is alkyl or aryl in pyridine at a temperature between about 0° and 100° C. to yield (c) the acylated compound of the formula

wherein A' is selected from a $$4'-(-O-\overset{O}{\underset{\|}{C}}R)-1'\text{-naphthyl}$$

moiety substituted in the 3'-position with a group,

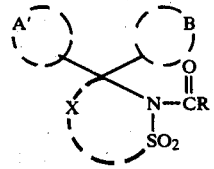

wherein R, $R^I$ and $R^{II}$ have the same meaning given above and a

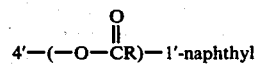

moiety substituted in the 3'-position with a group,

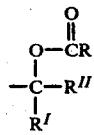

wherein R, $R^I$ and $R^{II}$ have the same meaning given above and B and X have the same meaning given above and (2) treating said compound (c) with alkali to give (d) the compound of the formula

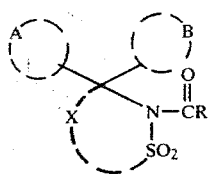

wherein A, B, X and R have the same meaning given above. Preferably, the halo substituents of said perhalomethyl are fluoro and/or chloro.

It will be understood that the 3,3-substituents and/or the ring-closing moiety of the compounds produced according to the subject method may contain one or more substituents in addition to those specified, which substituents should not interfere with the intended use of the compounds.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenethyl, phenylhexyl and phenyldodecyl; alkoxy, such as, methoxy, ethoxy, butoxy, octadecyloxy, 1-ethoxy-2-($\beta$-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichloromethyl; sulfonamido (—NH—SO$_2$R° wherein R° is alkyl, aryl, alkaryl or aralkyl); sulfamoyl (—SO$_2$—NH—R° wherein R° has the same meaning given above); acyl

wherein R° has the meaning given above); sulfonyl (—SO$_2$—R° wherein R° has the same meaning given above); sulfo; cyano; carboxy; hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino or a fused heretocyclic ring system, e.g., quinolizidine).

In a preferred embodiment, the method of the present invention comprises (1) reacting (a) a compound of the formula

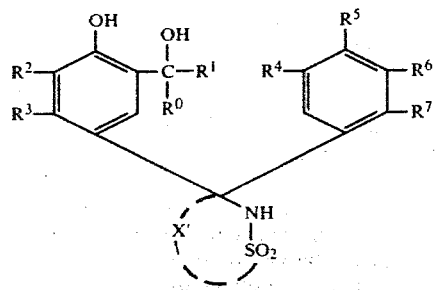

wherein R$^0$ is perhalomethyl selected from trifluoromethyl, difluoromethyl, difluorochloromethyl, dichlorofluoromethyl, dichloromethyl and trifluoromethyl; R$^1$ is selected from hydrogen and perhalomethyl having the same meaning given above; R$^2$ is hydrogen or methyl; R$^3$ is hydrogen, alkyl or alkoxy; R$^2$ and R$^3$ taken together represent the carbon atoms necessary to complete a fused benzene ring; R$^4$ and R$^6$ each are hydrogen, alkyl, alkoxy, chloro or fluoro; R$^5$ is hydrogen, alkyl, alkoxy, —OP$^I$ wherein P$^I$ is a protecting group, —N,N—(dialkyl)amino, —N,N—(w-R$^8$alkyl)$_2$amino wherein R$^8$ is halo or —OP$^{II}$ wherein P$^{II}$ is a protecting group; —NHCOCH$_3$, piperidino, pyrrolidino, N-methylpiperazino, morpholino, thiomorpholino or tetrahydro-2H,4H-1,3-6-dioxazocino; R$^7$ is hydrogen, alkyl, alkoxy or —OP$^{III}$ wherein P$^{III}$ is a protecting group usually the same as P$^I$ or P$^{II}$; R$^6$ and R$^7$ taken together represent the carbon atoms necessary to complete a fused benzene ring provided R$^2$ and R$^3$ are taken separately when R$^6$ and R$^7$ are taken together; R$^4$, R$^5$ and R$^6$ taken together represent the atoms necessary to complete a fused [ij]quinolizidine ring; and X' represents the atoms necessary to complete 2,3-dihydrobenz[d]isothiazole-1,1-dioxide or 2,3-dihydronaphtho[1,8-de]-1,2-thiazine-1,1-dioxide and (b) an acid halide of the formula

wherein W is chloro or bromo and R is alkyl or aryl in pyridine at a temperature between about 0° and 100° C. to yield (c) the triacylated compound of the formula

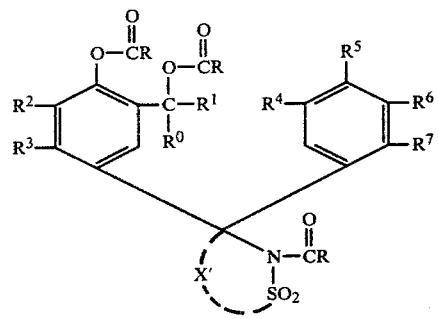

wherein R$^0$, R$^1$, R$^2$, R$^3$, R$^4$, R$^5$, R$^6$, R$^7$, X' and R have the same meaning given above; and (2) treating said compound (c) with 0.01 to 2.0 N base at a temperature between about 0° and 40° C. to yield (d) the compound having the formula

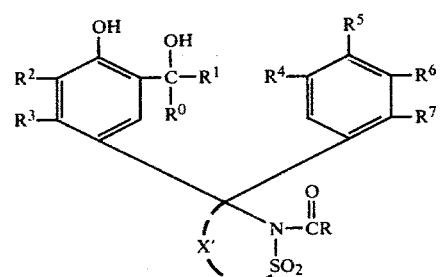

wherein R, $R^0$, $R^1$, $R^2$, $R^3$, $R^4$, $R^5$, $R^6$, $R^7$ and X' have the same meaning given above.

Where $R^5$ is —$OP^I$ or —N,N—(w—$OP^{II}$-alkyl)$_2$ and/or $R^7$ is $OP^{III}$, the compound (d) is treated with organic or inorganic acid at a pH between about 0.1 and 5.0 at a temperature between about 20° and 100° C. to remove the respective protecting groups.

Usually, the alkyl and alkoxy substituents comprising $R^3$, $R^4$, $R^5$, $R^6$ and $R^7$ are lower alkyl having 1 to 4 carbon atoms, such as, methyl, ethyl, n-propyl, isopropyl and n-butyl and lower alkoxy having 1 to 4 carbon atoms, such as, methoxy, ethoxy, propoxy and butoxy. Also, the alkyl groups of the —N,N-(dialkyl)amino each are usually alkyl containing 1 to 4 carbon atoms; the alkyl groups of the —N,N—(w—$R^8$alkyl)$_2$amino usually are lower alkyl having 1 to 4 carbon atoms; and $R^8$, when halo, is preferably chloro. The perhalomethyl groups comprising $R^0$ and $R^1$ may be the same or different and usually are the same.

Usually, R of said

when alkyl contains 1 to 7 carbon atoms, for example, methyl, ethyl, isopropyl, s-butyl, n-butyl, hexyl or benzyl and preferably, is methyl, and when aryl, preferably is phenyl.

In a particularly preferred embodiment, X' represents the atoms necessary to complete 2,3-dihydrobenz[d]-isothiazole-1,1-dioxide.

The above reaction scheme is illustrated below using as specific reactants, 3-[(3'-α-hydroxy-α-trifluoromethyl-β,β,β-trifluoroethyl)-4'-hydroxy-1'-naphthyl]-3-(9'-julolidinyl)-2,3-dihydrobenz[d]isothiazole-1,1-dioxide and acetyl chloride.

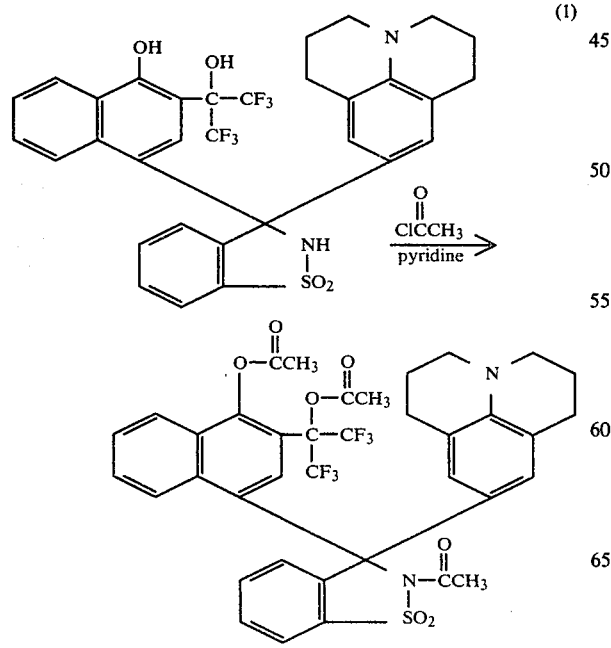

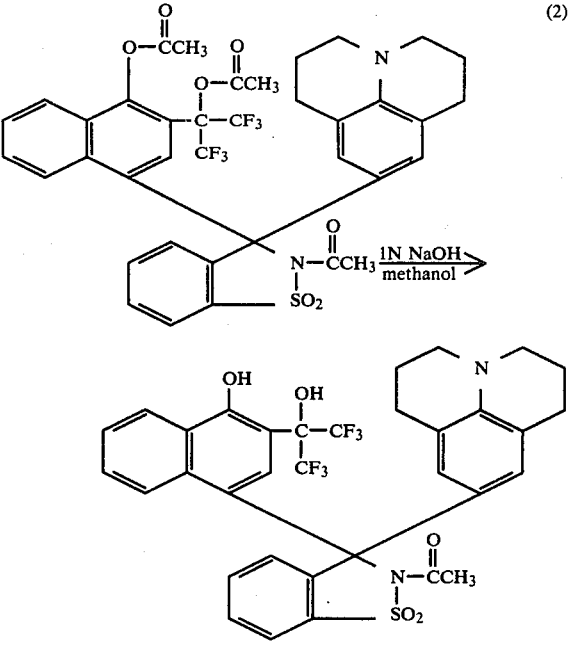

The novel intermediates of the present invention may be represented by the formula

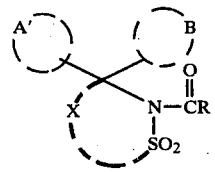

wherein A', B, X and R have the same meaning given above, and in a preferred embodiment may be represented by the formula

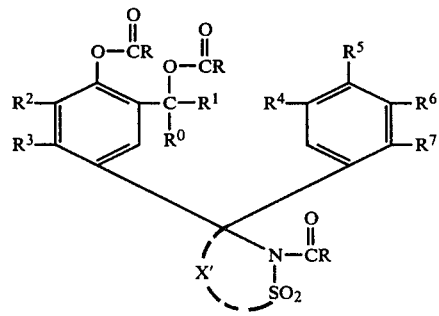

wherein $R^0$ is perhalomethyl selected from trifluoromethyl, difluoromethyl, difluorochloromethyl, dichlorofluoromethyl, dichloromethyl and trifluoromethyl; $R^1$ is selected from hydrogen and perhalomethyl having the same meaning given above; $R^2$ is hydrogen or methyl; $R^3$ is hydrogen, alkyl or alkoxy; $R^2$ and $R^3$ taken together represent the carbon atoms necessary to complete a fused benzene ring; $R^4$ and $R^6$ each are hydrogen, alkyl, alkoxy, chloro or fluoro; $R^5$ is hydrogen, alkyl, alkoxy, —$OP^I$ wherein $P^I$ is a protecting group, —N,N-(dialkyl)amino, —N,N-(w-$R^8$alkyl)-

$_2$amino wherein $R^8$ is halo or —$OP^{II}$ wherein $P^{II}$ is a protecting group; —$NHCOCH_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —$OP^{III}$ wherein $P^{III}$ is a protecting group usually the same as $P^I$ or $P^{II}$; $R^6$ and $R^7$ taken together represent the carbon atoms necessary to complete a fused benzene ring provided $R^2$ and $R^3$ are taken separately when $R^6$ and $R^7$ are taken together; $R^4$, $R^5$ and $R^6$ taken together represent the atoms necessary to complete a fused [ij]quinolizidine ring; and $X'$ represents the atoms necessary to complete 2,3-dihydrobenz[d]isothiazole-1,1-dioxide or 2,3-dihydronaphtho[1,8-de]-1,2-thiazine-1,1-dioxide and R is alkyl or aryl.

Certain of the N-acylated sulfamphthaleins and sulfamnaphthaleins produced in accordance with the subject method are among those forming the subject matter of copending U.S. Patent Application Ser. No. 957,163 of James W. Foley filed concurrently herewith, and as discussed therein find utility, for example, as light-screening dyes in photography.

By "sulfamphthalein" is intended a 2,3-dihydrobenz[d]isothiazole-1,1-dioxide moiety and by "sulfamnaphthalein" is intended as 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

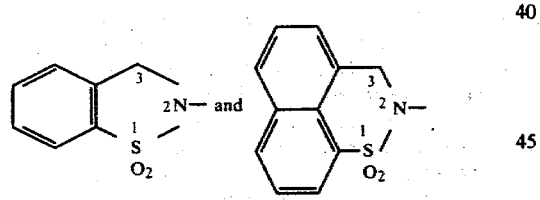

Specific examples of compounds that may be prepared according to the subject method are as follows:

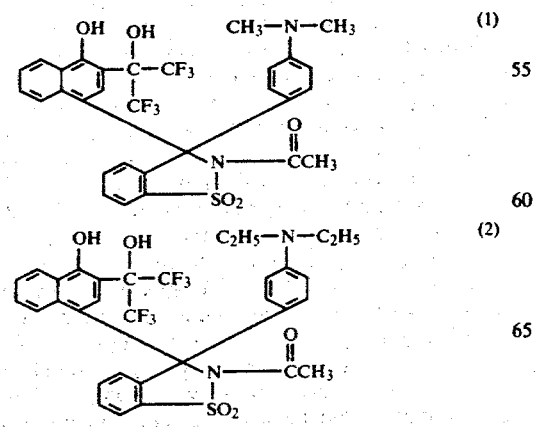

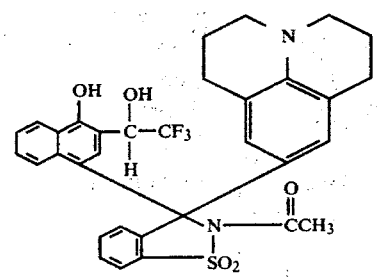

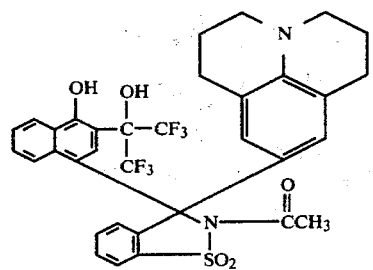

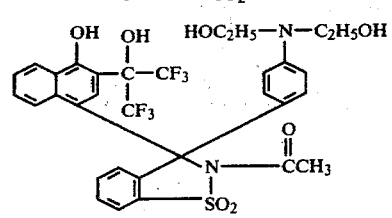

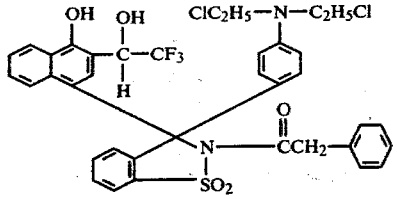

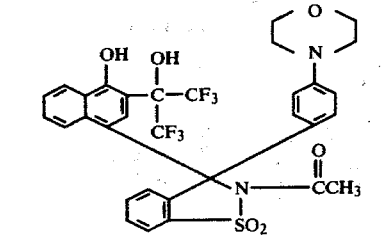

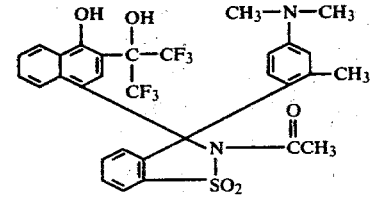

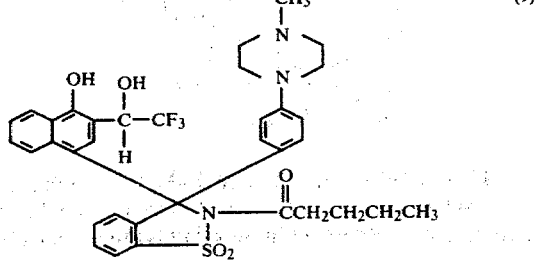

-continued

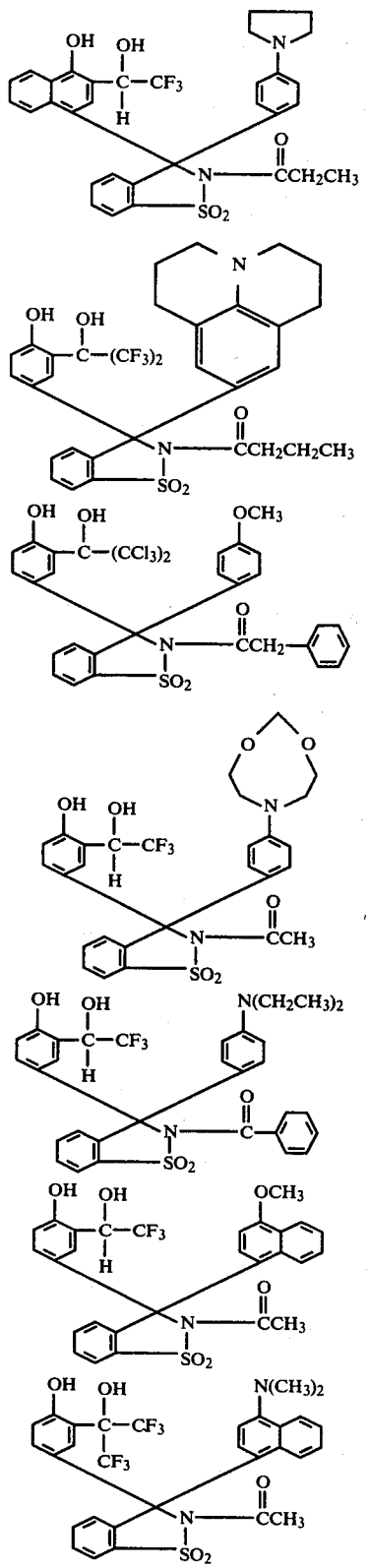

The 3,3-disubstituted-2,3-dihydrobenz[d]isothiazole-1,1-dioxides used as starting materials in the subject method may be prepared by reacting (a) the "lithiated" derivative of the perhalomethylcarbinol-substituted phenol or 1-naphthol, for example,

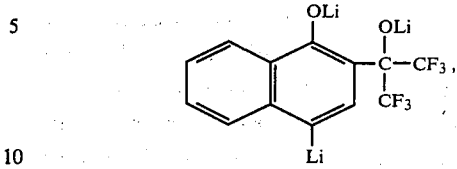

and (b) a 3-(phenyl)benz[d]isothiazole-1,1-dioxide wherein the 3-(phenyl) substituent may be substituted or unsubstituted in an inert organic solvent at between about −80° and 50° C. to give (c)

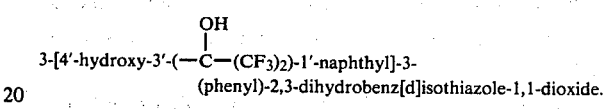

3-[4'-hydroxy-3'-(—C—(CF$_3$)$_2$)-1'-naphthyl]-3-(phenyl)-2,3-dihydrobenz[d]isothiazole-1,1-dioxide.

This method of reacting the "lithiated" perhalomethylcarbinolsubstituted phenol or 1-naphthol and the 3-(phenyl)benz[d]-isothiazole-1,1-dioxide and the products produced form the subject matter of copending U.S. patent application Ser. No. 956,908 of Louis Cincotta and James W. Foley filed concurrently herewith, which specification, for convenience, is specifically incorporated herein. As discussed therein, the 3-substituted-benz[d]isothiazole-1,1-dioxides reacted with the "lithiated" phenol (or 1-naphthol) reagent may be a 3-(4'-OP-1'-phenyl/4'-OP-1'-naphthyl)-benz[d]-isothiazole-1,1-dioxide or a 3-(phenyl/naphthyl)benz[d]-isothiazole-1,1-dioxide wherein the 3-(phenyl/naphthyl) substituent may be unsubstituted or substituted with other than a 4'-OP substituent.

When 3-(4'-OP-1'-phenyl/4'-OP-1'-naphthyl)benz[d]-isothiazole-1,1-dioxides are employed, they are prepared by blocking the functional hydroxy group and any substituent group(s), as may be appropriate, of the selected 4-halophenol or 4-halo-1-naphthol and converting the blocked phenol or 1-naphthol to the corresponding Grignard or lithium reagent which is then reacted with a saccharin reagent. The 4-halo substituent may be chloro, bromo or iodo when the lithium reagent is prepared by reacting the blocked phenol or blocked 1-naphthol with lithium metal and is either bromo or iodo when the lithium reagent is made via a lithium exchange reaction using, for example, n-butyllithium. In preparing the Grignard reagent by reacting the blocked phenol or 1-naphthol with magnesium metal, the 4-halo substituent may be chloro, bromo or iodo. The Grignard or lithium reagent thus prepared is then reacted with saccharin, the N-lithium salt of saccharin or saccharin pseudo-chloride to yield the corresponding 3-(4'-OP-1'-phenyl/4'-OP-1'-naphthyl)benz[d]isothiazole-1,1-dioxide. Generally, the Grignard reagent is reacted with the pseudo-chloride, and the lithium reagent is reacted with the N-lithium salt. The 3-(4'-OP-1'-phenyl/4'-OP-1'-naphthyl)naphtho[1,8-de]-1,2-thiazine-1,1-dioxides may be prepared in a similar manner by reacting the Grignard or lithium reagent with 2,3-dihydro-3-oxo-naphtho[1,8-de]-1,2-thiazine-1,1-dioxide, its pseudo-chloride or the N-lithium derivative thereof.

The groups selected for protecting the functional phenolic or naphtholic hydroxy group and other hydroxy groups that may be present in the phenol or 1-naphthol should be stable to and compatible with organolithium and Grignard reagents and should protect the hydroxy group(s) against reaction under the conditions encountered in preparing the starting materials for the subject method. It will be appreciated that starting materials without protecting groups on the 3-(4'-OH-1'-phenyl/4'-OH-1'-naphthyl) moiety may be employed in the subject acylation reaction since the acyl groups can be removed simultaneously with the acyl groups on the perhalomethylcarbinol-substituted moiety. However, it is more convenient to leave the protecting group(s) on the starting materials derived fro m the 3-(4'-OP-1'-phenyl/4'-OP-1'-naphthyl)benz[d]isothiazole-1,1-dioxides and remove the protecting groups subsequent to the acylation reaction. Thus, the protecting group selected should be capable of being easily removed under weakly acid conditions to regenerate the hydroxy group(s) without the removal of or adversely affecting the N-substituent or other substituents that may be present. Alkyl groups, such as methyl and ethyl, may be employed in those instances where they can be removed without removal of the N-substituent. Because they can be readily removed without disturbing the N-substituent or other substituents, the phenol or 1-naphthol preferably is protected with methoxymethyl, 2'-tetrahydropyranyl or dimethyl-t-butylsilyl. The blocked phenols and 1-naphthols employing these protecting groups may be prepared by methoxymethylation as described, for example, by Kaoru Fuji et al, Synthesis, 4, pp. 276–277 (1975), by tetrahydropyranylation as described, for example, by William E. Parham et al, *J. Amer. Chem. Soc.*, 70, pp. 4187–4189 (1948) or by silylating with dimethyl-t-butylsilyl chloride in the presence of imidazole as described by E. J. Corey et al, *J. Amer. Chem. Soc.*, 94, pp. 6190–6191 (1972).

When 3-(phenyl/naphthyl)-benz[d]isothiazole-1,1-dioxides are employed, i.e., other than 3-(phenyl/naphthyl) compounds containing a 4'-OP-substituent, they may be prepared in a similar manner by blocking hydroxy and/or other substituent group(s), as may be appropriate, of the selected halo-benzene or halo-naphthalene compound and converting the halo commpound to the corresponding Grignard or lithium reagent which is then reacted with the saccharin reagent to give the corresponding 3-substituted-benz[d]-isothiazole-1,1-dioxide.

Certain 3-(4'-OP-1'-phenyl/4'-OP-1'-naphthyl)benz[d]isothiazole-1,1-dioxides form the subject matter of copending U.S. patent application Ser. No. 836,024 of Alan L. Borror, L. Cincotta, E. W. Ellis, J. W. Foley and M. M. Kampe filed Sept. 23, 1977 now U.S. Pat. No. 4,181,660. 3-(phenyl/naphthyl)benz[d]isothiazole-1,1-dioxides substituted with certain N-heterocyclic moieties form the subject matter of copending U.S. patent application Ser. No. 836,022 of Alan L. Borror, J. W. Foley and J. W. Lee, Jr. filed Sept. 23, 1977, now U.S. Pat. No. 4,139,704, and 3-(9'-julolidinyl)benz[d]isothiazole-1,1-dioxide forms the subject matter of copending U.S. patent application Ser. No. 836,023 also filed Sept. 23, 1977 now U.S. Pat. No. 4,140,689.

The "lithiated" derivative of the perhalomethylcarbinol-substituted phenol or 1-naphthol is prepared by reacting the selected 4-halophenol or 4-halo-1-naphthol with at least three molar equivalents of lithium metal or preferably, n-butyllithium in an inert organic solvent at a temperature between about −50° and −70° C. as illustrated below

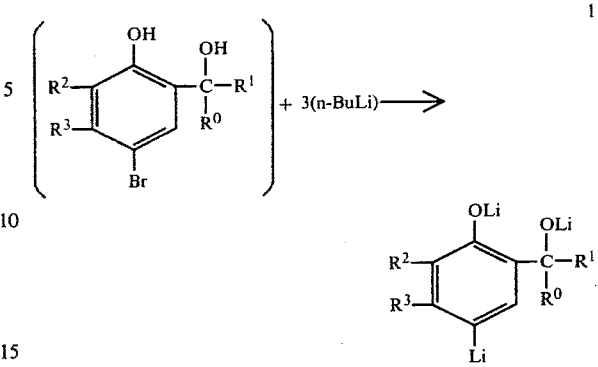

The perhalomethylcarbinol-substituted phenols and 1-naphthols may be prepared according to the procedures set forth by Basil F. Farah et al. *J. Org. Chem.*, Vol. 30, p. 1003 (1965) and are halogenated in any conventional manner to give the 4-halo derivatives, for example, by reacting the perhalomethyl-carbinol-substituted compound with chloride or bromine, with or without a catalyst; N-bromosuccinimide or iodinemonochloride.

In carrying out the subject method, the selected 3,3-substituted-2,3-dihydrobenz[d]isothiazole-1,1-dioxide as prepared above is reacted with at least three molar equivalents of an acid halide of the formula

wherein W is chloro or bromo and R has the same meaning given above in pyridine solution to give the acylated compound. About 3 to 6 moles of acid halide may be used for each mole of the 3,3-disubstituted-2,3-dihydrobenz[d]isothiazole-1,1-dioxide depending upon the number of unblocked —OH groups present in addition to the

of the isothiazole ring, and usually 5 to 6 moles are employed. Since the reaction is exothermic, external heating may be unnecessary, but the reaction mixture may be heated to facilitate completion of the reaction, if desired. Ordinarily, the reaction temperature ranges between about 0° and 100° C., and if desired, the reaction may be conducted in an inert atmosphere, for example, under nitrogen.

Carboxylic acid halides are well known and may be prepared in a conventional manner, for example, by reacting the selected carboxylic acid, RCOOH, with phosphorus trichloride, phosphorus pentachloride or thionyl chloride to give the corresponding RCOCl.

The acyl groups,

are removed from the 4'-hydroxy and carbinol hydroxy groups of the acylated 3-(4'-hydroxy-3'-perhalomethylcarbinol-1'-phenyl/4'-hydroxy-3'-perhalomethylcarbinol-1'-naphthyl) substituent of the sulfam(na)phthalein by treating with 0.01 to 2.0 N base at a temperature between about 0° and 40° C., and usually room temperature. The base may be, for example, methylamine but preferably is an ionic hydroxide base, such as, tetrabutylammonium hydroxide, sodium hydroxide or potassium hydroxide in a solvent, such as, water and/or a lower alkanol, e.g., methanol and ethanol.

As mentioned above, any protecting groups, P, as may be present in the other 3-substituent of the sulfam(na)phthalein are removed by treating the N-acylated compound with acid having a pH between about 0.1 and 5.0 at a temperature between about 20° and 100° C. The acid may be an inorganic acid, such as, hydrochloric acid or sulfuric acid in a protic solvent, e.g., water, alkanol, such as, methanol or ethanol, or aqueous alkanol, or the acid may be an organic acid, such as, acetic acid or trifluoroacetic acid alone or in a protic solvent, such as those mentioned above.

The following examples are given to further illustrate the present invention and are not intended to limit the scope thereof.

EXAMPLE 1

Preparation of the compound having the formula

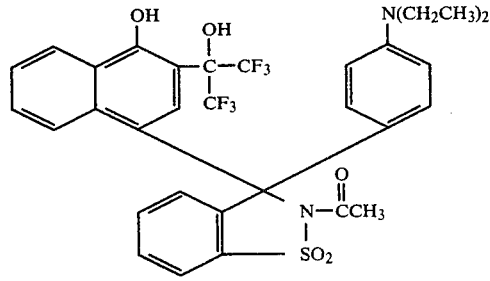

(a) 4-Bromo-2-(α-hydroxy-α-trifluoromethyl-β,β,β-trifluoroethyl)-1-naphthol (1.0 g) was dissolved in 20 ml of anhydrous tetrahydrofuran at room temperature. The solution was then cooled to −65° C., and 3.21 ml of n-butyllithium (2.4 M in hexane) was added dropwise (an exotherm occurred during approximately 1 ml of the addition). The resulting light yellow solution was then stirred for one hour at −65° C. To the solution was added 0.81 g of 3-(4'-N,N-diethylamino-1'-phenyl)-benz[d]-isothiazole-1,1-dioxide. The reaction solution was allowed to warm to −40° C. then poured into 200 ml of water, made pH 6 with conc. HCl and extracted with ether. The ether was then washed with 200 ml of 1 N sodium hydroxide. The sodium hydroxide solution was separated, washed with ether, then neutralized with HCl. The neutralized solution was extracted with ether, the ether dried over sodium sulfate and evaporated to leave a light green solid. Preparative TLC on silica gel with ether gave 0.5 g of 3-[(3'-α-hydroxy-α-trifluoromethyl-β,β,β-trifluoroethyl)-4'-hydroxy-1'-naphthyl]-3-[4'-N,N-diethylamino-1'-phenyl]-2,3-dihydrobenz[d]isothiazole-1,1-dioxide. (b) The compound prepared in step (a) (0.5 g) was dissolved in 25 ml of pyridine and 2 ml of acetylchloride was added dropwise at room temperature. The reaction solution was stirred for 6 hours, poured into 500 ml of water, and the tan precipitate was filtered, washed well with water and vacuum dried.

(c) The triacetylated compound prepared in step (b) was dissolved in 100 ml of methanol and 5 drops of 50% aqueous sodium hydroxide solution was added. The resulting purple solution was stirred for 2 hours. TLC on silica gel with ether showed that de-acetylation of the —OH groups was complete. The methanol was removed under vacuum. After neutralization with HCl, chloroform was added to the residue and sodium sulfate for drying. The solution was filtered and the chloroform evaporated to leave 0.584 g of the title compound as a cyan solid.

The 3-(4'-N,N-diethylamino-1'-phenyl)benz[d]-isothiazole-1,1-dioxide was prepared as follows:

4-Bromo-N,N-diethylaniline (22.8 g) was dissolved in 100 ml of anhydrous tetrahydrofuran under nitrogen and then cooled to −74° C. To this solution was added dropwise 41.8 ml of n-butyllithium (2.4 M in hexane) over a 50-minute period. (The temperature was maintained at −70° C. during the addition). The solution was stirred for one hour. Then a solution of the N-lithium salt of saccharin in 100 ml of tetrahydrofuran was added dropwise to the aniline solution at −70° C. using a double ended needle. The resulting reaction mixture was stirred for 4 hours, poured slowly into 1 liter of water and the pH adjusted to 6 with conc. HCl. An orange precipitate formed which was filtered, dried and dissolved in 250 ml of methanol containing about 5 ml of conc. HCl. The solution was refluxed for 30 minutes and the precipitate collected to give 14.0 g of the title compound (melting range 207°–208° C.).

EXAMPLE 2

Preparation of the compound having the formula

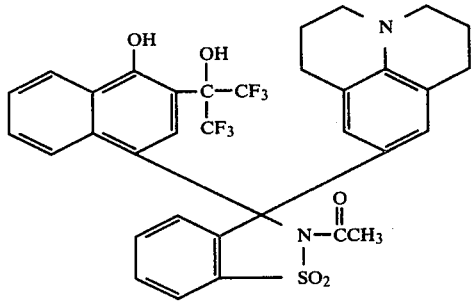

The title compound was prepared according to the procedure described in Example 1 above except that 4-bromo-2-(α-hydroxy-α-trifluoromethyl-β,β,β-trifluoroethyl)-1-naphthol and 3-(9'-julolidinyl)benz[d]isothiazole-1,1-dioxide were employed in step (a).

The 3-(9'-julolidinyl)benz[d]isothiazole-1,1-dioxide was prepared as follows:

(a) 134 g (0.758 mol) of 98% julolidine was dissolved in 500 ml of glacial acetic acid. To this solution was added a solution of 121 g (0.758 mol) of bromine in 22400 ml of glacial acetic acid. After the addition, the reaction mixture was stirred for 15 minutes and then tested for excess bromine using KI paper. More bromine was added until an excess was detected. The reaction mixture was then stirred for 1 hour at room temperature. The pink solid which formed was collected and washed several times with ether and dried in a vacuum oven overnight to give 245 g of the hydrobromide salt of 9-bromojulolidine. Yield 92% by weight.

(b) 75 g (0.22 mol) of 9-bromojulolidine hydrobromie prepared in step (a) was suspended in 1200 ml of ether. To the suspension was added 650 ml of 1 N sodium hydroxide and the mixture stirred for 5–10 minutes. The two layers were separated and the aqueous layer was extracted with 1000 ml of ether. The organic layers were combined, dried over anhydrous calcium sulfate and the ether evaporated to yield 51.97 g (0.206 mol) of 9-bromojulolidine as a dark oil.

(c) The 9-bromojulolidine was dissolved in 400 ml of dry tetrahydrofuran under nitrogen at −65° C. 85.8 ml of n-butyllithium (2.4 M in hexane) was added dropwise giving a tan slurry.

(d) 37.75 g (0.206 mol) of saccharin was dissolved in 400 ml of dry tetrahydrofuran under nitrogen at −65° C. 85.8 ml (0.206 mol) of n-butyllithium (2.4 M in hexane) was added dropwise until a permanent orange colored endpoint was reached. The mixture was stirred for 1 hour at −65° C. and then used directly in step (e).

(e) The mixture of step (d) was added to the tan slurry of step (c) at −60° C. to −50° C. through a double ended needle. After the addition was completed, the reaction mixture was stirred for 1 hour at −60° C. and gradually warmed to room temperature. The reaction mixture was then poured into 800 ml of water and the pH adjusted to 5–6 with conc. HCl. The orange precipitate which formed was collected to give 13.9 g of the title compound. The filtrate was extracted with ether, dried and evaporated to give 46 g of a dark oil. The oil was washed with hot hexane and then dissolved in hot ethanol (500 ml) and 75 drops of conc. HCl was added. The ethanol was cooled and 7.53 g of orange crystals were collected to give the title compound in a total yield of 21.47 g.

EXAMPLE 3

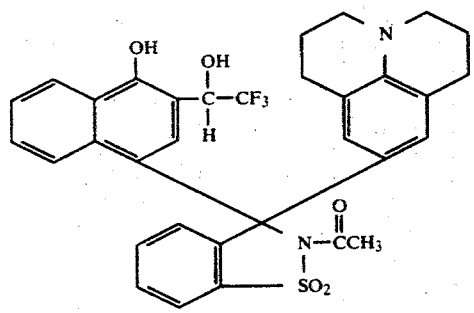

The title compound was prepared according to the procedure described in Example 1 above except that 4-bromo-2-(α-hydroxy-β,β,β-trifluoroethyl)-1-naphthol and 3-(9′-julolidinyl)benz[d]isothiazole-1,1-dioxide were employed in step (a).

EXAMPLE 4

Preparation of the compound having the formula

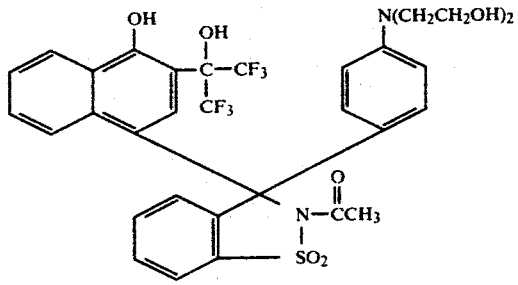

The title compound was prepared according to the procedure described in Example 1 above except that 4-bromo-2-(α-hydroxy-α-trifluoromethyl-β,β,β-trifluoroethyl)-1-naphthol and 3-[4′-N,N-di(α-2″-tetrahydropyranyloxyethyl)-1′-phenyl]benz[d]isothiazole-1,1-dioxide were employed in step (a) and the tetrahydropyranyl protecting groups were removed subsequent to deacetylation of the hydroxy groups by refluxing in methanol made acidic with conc. HCl for about one hour.

The 3-[4′-N,N-di(β-2″-tetrahydropyranyloxyethyl)-1′-phenyl]benz[d]isothiazole-1,1-dioxide were prepared as follows:

4-Bromo-N,N-di(β-2′-tetrahydropyranyloxyethyl)aniline (10.0 g) was dissolved in 100 ml of tetrahydrofuran. The solution was cooled to −65° C. and 10 ml of n-butyllithium (2.4 M in hexane) was added dropwise under nitrogen at a rate to maintain the temperature below −65° C.

In a separate flask, saccharin (4.28 g) was dissolved in 50 ml of tetrahydrofuran under nitrogen, and the solution was cooled to −65° C. n-Butyllithium (2.4 M in hexane) was added until a peach color persisted (about 9.0 ml).

The latter solution of the N-lithium salt of saccharin was added to the aniline solution by hollow wire over a 10 minute period. (Initially a green color formed which changed to tan.) The reaction mixture was stirred for 1.5 hours and poured into 2 liters of water. The pH was adjusted to 6 with conc. HCl, and the mixture extracted with ether. The ether extract was dried and evaporated and the residue was dissolved in 100 ml of toluene. Two spatula tips of toluene sulfonic acid monohydrate were added, and the solution was refluxed for about 6 hours. The toluene was evaporated and the residue was dissolved in 2 liters of ether. The ether solution was cooled and the crystalline solid was collected to give 4.0 g of the title compound (melting range 100°–101° C.).

Tetrahydropyranylation of p-Br-N,N-di(β-hydroxyethyl)-aniline was carried out as follows:

p-Br-N,N-di(β-hydroxyethyl)aniline (20.0 g) was dissolved in 475 ml of dichloromethane containing 60 ml of dihydropyran. To this solution was added 1 ml of conc. HCl, and the reaction solution was stirred for about 5.5 hours. The solution was then washed with water containing enough sodium hydroxide to neutralize any acid present. The dichloromethane was separated, dried over anhydrous sodium sulfate and evaporated under reduced pressure with a steam bath (aspirator) leaving an oil. The oil was heated to 115° C. at 0.1 mm Hg to distill off impurities leaving 33.0 g of the title compound. 4-Bromo-2-(α-hydroxy-α-trifluoromethyl-β,β,β-trifluoroethyl)-1-naphthol was prepared by adding a suspension of 50 g (0.161 mole) of 2-(α-hydroxy-α-trifluoromethyl)-1-naphthol in 500 ml of CCl₄ to a 3-necked, 2-liter flask equipped with a mechanical stirrer. This suspension was stirred while a solution of 8.5 ml (0.161 mole) Br₂ in 200 ml CCl₄ was added dropwise. Upon completion of the addition, the mixture was stirred for 2 hours, then filtered, and the filtrate evaporated under reduced pressure to leave a tan solid. This solid was dissolved with heating on a steam bath into 300 ml of ligroin (b.p. 90°–110° C.). 10 Grams of norit was added, heating was continued for a further 10 minutes, and then the mixture was filtered through a sintered glass funnel containing a celite pad. Upon cooling and filtration, 50 g of white crystals were collected (melting range 116°–117° C.) The mother liquor was concentrated to one-half the original volume and a second crop of 5 g (melting range 112°–115° C.) was collected to give a total yield of 55 g (88%).

EXAMPLE 5

Preparation of the compound having the formula

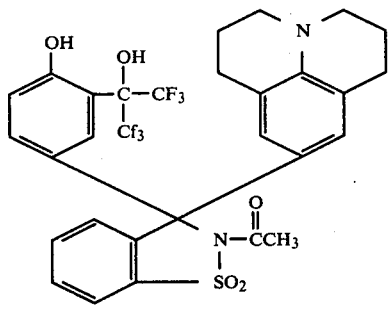

The title compound was prepared according to the procedure given in Example 1 above except that 4-bromo-2-(α-hydroxy-α-trifluoromethyl-β,β,β-trifluoroethyl)-1-phenol and 3-(9'-julolidinyl)benz[d]isothiazole-1,1-dioxide were employed in step (a).

EXAMPLE 6

Preparation of the compound having the formula

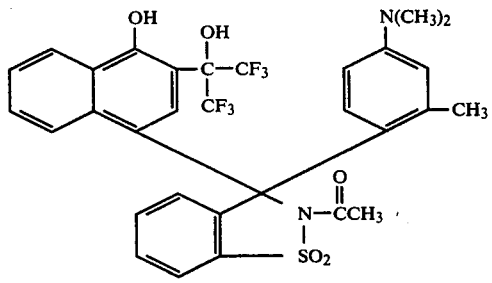

The title compound was prepared according to the procedure given in Example 1 above except that 4-bromo-2-(α-hydroxy-α-trifluoromethyl-β,β,β-trifluoroethyl)-1-naphthol and 3-(4'-N,N-dimethylamino-2'-methyl-1'-phenyl)benz[d]-isothiazole-1,1-dioxide were employed in step (a).

EXAMPLE 7

Preparation of the compound of the formula

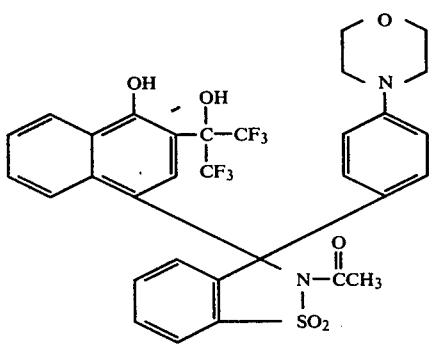

The title compound was prepared according to the procedure given in Example 1 above except that 4-bromo-2-(α-hydroxy-α-trifluoromethyl-β,β,β-trifluoroethyl)-1-naphthol and 3-(4'-N-morpholinyl-1'-phenyl)benz[d]isothiazole-1,1-dioxide were employed in step (a).

Where it is desired to prepare sulfamnaphthaleins, it will be appreciated that 2,3-dihydro-3-oxo-naphtho[1,8-de]-1,2-thiazine-1,1-dioxide or its pseudo-chloride may be substituted for the saccharin reagents used in the foregoing Examples to give the corresponding sulfamnaphthalein intermediates and products. The pseudo-chloride may be prepared from the 3-oxo thiazine by reaction with $PCl_5$.

The 3,3-disubstituted-sulfamphthaleins and sulfamnaphthaleins produced by the subject method are useful as pH-sensitive indicator dyes and have reversibly alterable spectral absorption characteristics in response to changes in environmental pH. Besides their use in titrations and other analytical procedures where pH-sensitive indicator dyes are commonly employed, the compounds having a colorless form below a given pH may be used for providing colored optical filter agents in photographic products and processes where the pH is reduced subsequent to processing as described in U.S. Pat. No. 3,647,437 issued Mar. 7, 1972 to Edwin H. Land. This patent is concerned with diffusion transfer processes wherein the resulting photograph comprises the developed photosensitive layer(s) retained with the image-receiving layer as part of a permanent laminate. In the processes disclosed, a photographic film unit comprising a photosensitive element is developed in ambient light but further undesired exposure during processing is prevented by a light-absorbing material or optical filter agent which is retained in the processed film unit. In a preferred embodiment, the optical filter agent is a pH-sensitive dye, i.e., a dye possessing spectral absorption characteristics that are reversibly alterable in response to changes in environmental pH and particularly, a pH-sensitive dye having a colored or light-absorbing form above a given alkaline pH and a colorless or non-light-absorbing form below said pH. Though the pH-sensitive dye is usually included in the processing composition, it may be initially positioned in the film unit, for example, in a layer over the photosensitive element provided it is in its colorless form if photoexposure is to be effected through that layer. Upon application of an alkaline processing composition, the pH-sensitive dye is converted to its colored form, and after the desired processing time, it is converted back to its colorless form by reducing the environmental pH, e.g., by including an acid-reacting layer as part of the film unit.

Since certain changes may be made in the above product and process without departing from the scope of the invention herein involved, it is intended that all matter contained in the above description shall be interpreted as illustrative and not in a limiting sense.

What is claimed is:
1. A method which comprises (1) reacting (a) a compound of the formula

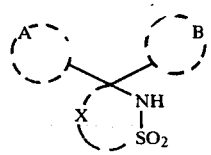

wherein A is selected from a 4'-hydroxy-1'-naphthyl moiety substituted in the 3'-position with a group,

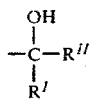

wherein $R^I$ is perhalomethyl and $R^{II}$ is hydrogen or perhalomethyl and a 4'-hydroxy-1'-phenyl moiety substituted in the 3'-position with a group,

wherein $R^I$ is perhalomethyl and $R^{II}$ is hydrogen or perhalomethyl; B is a phenyl moiety or a naphthyl moiety provided B is a phenyl moiety when said A is said 4'-hydroxy-1'-naphthyl moiety and X represents the atoms necessary to complete a ring-closing moiety selected from a sulfamphthalein moiety and a sulfamnaphthalein moiety and (b) an acid halide of the formula

wherein W is chloro or bromo and R is alkyl or aryl in pyridine at a temperature between about 0° and 100° C. to yield (c) the acylated compound of the formula

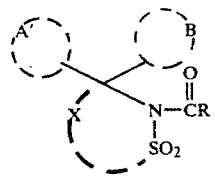

wherein A' is selected from a

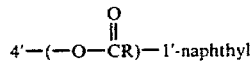

moiety substituted in the 3'-position with a group,

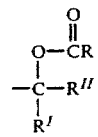

wherein R, $R^I$ and $R^{II}$ have the same meaning given above and a

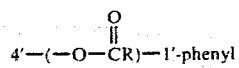

moiety substituted in the 3'-position with a group,

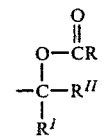

wherein R, $R^I$ and $R^{II}$ have the same meaning given above and B and X have the same meaning given above and (2) treating said compound (c) with alkali to give (d) the compound of the formula

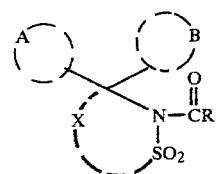

wherein A, B, X and R have the same meaning given above.

2. A method as defined in claim 1 wherein A is said 4'-hydroxy-1'-naphthyl moiety.

3. A method as defined in claim 1 wherein A is said 4'-hydroxy-1'-phenyl moiety.

4. A method as defined in claim 1 wherein R is alkyl.

5. A method as defined in claim 1 wherein R is aryl.

6. A method as defined in claim 1 wherein said halo of said perhalomethyl is selected from chloro and fluoro.

7. A method which comprises (1) reacting (a) a compound of the formula

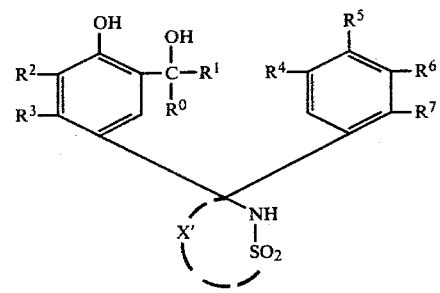

wherein $R^0$ is perhalomethyl selected from trifluoromethyl, difluoromethyl, difluorochloromethyl, dichlorofluoromethyl, dichloromethyl and trifluoromethyl; $R^1$ is selected from hydrogen and perhalomethyl having the same meaning given above; $R^2$ is hydrogen or methyl; $R^3$ is hydrogen, alkyl or alkoxy; $R^2$ and $R^3$ taken together represent the carbon atoms necessary to complete a fused benzene ring; $R^4$ and $R^6$ each are hydrogen, alkyl, alkoxy, chloro or fluoro; $R^5$ is hydrogen, alkyl, alkoxy, —$OP^I$ wherein $P^I$ is a protecting group, —N,N-(dialkyl)amino, —N,N-(w-$R^8$alkyl)$_2$amino wherein $R^8$ is halo or —$OP^{II}$ wherein $P^{II}$ is a protecting group; —NHCOCH$_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —$OP^{III}$ wherein $P^{III}$ is a protecting group usually the same as $P^I$ or $P^{II}$; $R^6$ and $R^7$ taken together represent the carbon atoms necessary to complete a fused benzene ring provided $R^2$ and $R^3$ are taken separately when $R^6$ and $R^7$ are taken together; $R^4$, $R^5$ and $R^6$ taken together represent the atoms necessary to complete a fused [ij]quinolizidine ring; and X' represents the atoms necessary to complete 2,3-dihydrobenz[d]isothiazole-1,1-dioxide or 2,3-dihydronaphtho[1,8-de]-1,2-thiazine-1,1-dioxide and (b) an acid halide of the formula

wherein W is chloro or bromo and R is alkyl or aryl in pyridine at a temperature between about 0° and 100° C. to yield (c) the triacylated compound of the formula

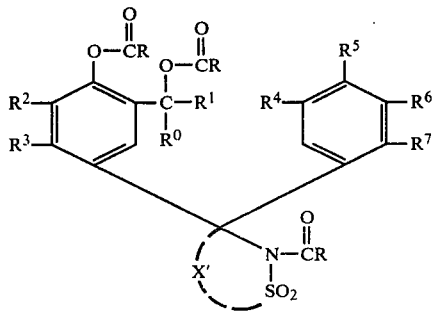

wherein $R^0$, $R^1$, $R^2$, $R^3$, $R^4$, $R^5$, $R^6$, $R^7$, X' and R have the same meaning given above; and (2) treating said compound (c) with 0.01 to 2.0 N base at a temperature between about 0° and 40° C. to yield (d) the compound having the formula

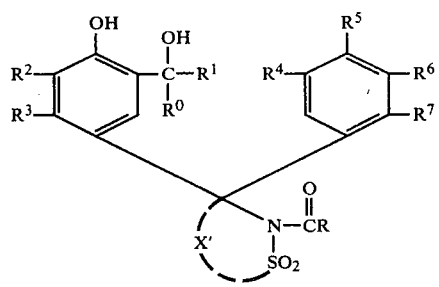

wherein R, $R^0$, $R^1$, $R^2$, $R^3$, $R^4$, $R^5$, $R^6$, $R^7$ and X' have the same meaning given above.

8. A method as defined in claim 7 wherein X' represents the atoms necessary to complete 2,3-dihydrobenz[d]isothiazole-1,1-dioxide.

9. A method as defined in claim 7 wherein $R^2$ and $R^3$ are hydrogen.

10. A method as defined in claim 7 wherein $R^2$ and $R^3$ taken together represent the carbon atoms necessary to complete a fused benzene ring.

11. A method as defined in claim 7 wherein $R^1$ is hydrogen.

12. A method as defined in claim 11 wherein $R^0$ is trifluoromethyl.

13. A method as defined in claim 7 wherein $R^1$ is perhalomethyl.

14. A method as defined in claim 13 wherein $R^0$ and $R^1$ are trifluormethyl.

15. A method as defined in claim 7 wherein $R^4$, $R^5$ and $R^6$ taken together represent the atoms necessary to complete a fused [ij]quinolizidine ring.

16. A method as defined in claim 7 wherein $R^4$, $R^6$ and $R^7$ are hydrogen.

17. A method as defined in claim 16 wherein $R^5$ is —N,N-dialkylamino.

18. A method as defined in claim 16 wherein $R^5$ is morpholino.

19. A method as defined in claim 7 wherein R is alkyl.

20. A method as defined in claim 7 wherein R is aryl.

21. A method as defined in claim 7 which additionally includes treating said (d) with acid having a pH between about 0.1 and 5.0 at a temperature between about 20° and 100° C. to remove said protecting groups $P^I$, $P^{II}$ and $P^{III}$.

22. A method as defined in claim 21 wherein $R^5$ is —N,N—(w—$R^8$alkyl)amino wherein $R^8$ is —$OP^{II}$ and $P^{II}$ is a protecting group.

23. A compound of the formula

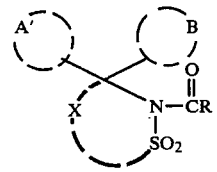

wherein A' is selected from a

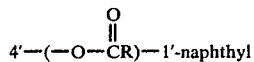

moiety substituted in the 3'-position with a group,

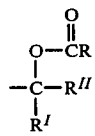

wherein R is alkyl or aryl, $R^I$ is perhalomethyl and $R^{II}$ is hydrogen or perhalomethyl and a

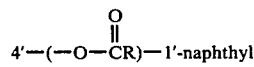

moiety substituted in the 3'-position with a group,

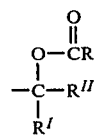

wherein R, $R^I$ and $R^{II}$ have the same meaning given above; B is a phenyl moiety or a naphthyl moiety provided B is a phenyl moiety when said A' is said

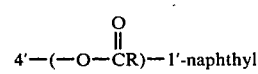

moiety and X represents the atoms necessary to complete a ring-closing moiety selected from a sulfamphthalein moiety and a sulfamnaphthalein moiety.

24. A compound as defined in claim 23 wherein X represents the atoms necessary to complete a sulfamphthalein moiety.

25. A compound as defined in claim 23 wherein A' is said

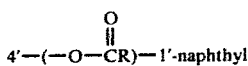

4'—(—O—CR)—1'-naphthyl moiety.

26. A compound as defined in claim 23 wherein B is said phenyl moiety.

27. A compound of the formula

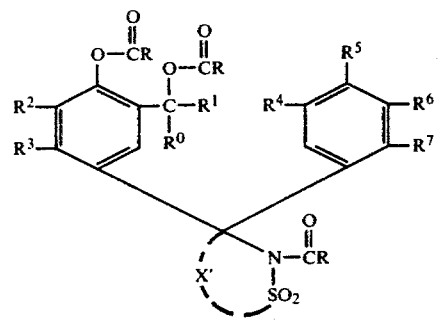

wherein $R^0$ is perhalomethyl selected from trifluoromethyl, difluoromethyl, difluorochloromethyl, dichlorofluoromethyl, dichloromethyl and trifluoromethyl; $R^1$ is selected from hydrogen and perhalomethyl having the same meaning given above; $R^2$ is hydrogen or methyl; $R^3$ is hydrogen, alkyl or alkoxy; $R^2$ and $R^3$ taken together represent the carbon atoms necessary to complete a fused benzene ring; $R^4$ and $R^6$ each are hydrogen, alkyl, alkoxy, chloro or fluoro; $R^5$ is hydrogen, alkyl, alkoxy, $-OP^I$ wherein $P^I$ is a protecting group, $-N,N$-(dialkyl)amino, $-N,N-$(w-$R^8$alkyl)$_2$amino wherein $R^8$ is halo or $-OP^{II}$ wherein $P^{II}$ is a protecting group; $-NHCOCH_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or $-OP^{III}$ wherein $P^{III}$ is a protecting group usually the same as $P^I$ or $P^{II}$; $R^6$ and $R^7$ taken together represent the carbon atoms necessary to complete a fused benzene ring provided $R^2$ and $R^3$ are taken separately when $R^6$ and $R^7$ are taken together; $R^4$, $R^5$ and $R^6$ taken together represent the atoms necessary to complete a fused [ij]quinolizidine ring; and X' repesents the atoms necessary to complete 2,3-dihydrobenz[d]isothiazole-1,1-dioxide or 2,3-dihydronaphtho[1,8-de]-1,1-dioxide and R is alkyl or aryl.

28. A compound as defined in claim 27 wherein X represents the atoms necessary to complete 2,3-dihydrobenz[d]-isothiazole-1,1-dioxide.

29. A compound as defined in claim 27 wherein $R^2$ and $R^3$ are hydrogen.

30. A compound as defined in claim 27 wherein $R^2$ and $R^3$ taken together represent the carbon atoms necessary to complete a fused benzene ring.

31. A compound as defined in claim 27 wherein $R^4$, $R^5$ and $R^6$ taken together represent the atoms necessary to complete a fused [ij]quinolizidine ring and $R^7$ is hydrogen.

32. A compound as defined in claim 27 wherein $R^4$, $R^6$ and $R^7$ are hydrogen.

33. A compound as defined in claim 32 wherein $R^5$ is $-N,N-$(dialkyl)amino.

34. A compound as defined in claim 32 wherein $R^5$ is $-N,N-$(w-$R^8$alkyl)$_2$amino.

35. A compound as defined in claim 32 wherein $R^5$ is morpholino.

36. A compound as defined in claim 27 wherein $R^4$ and $R^6$ are hydrogen, $R^5$ is $-N,N-$(dialkyl)amino and $R^7$ is alkyl.

37. The compound

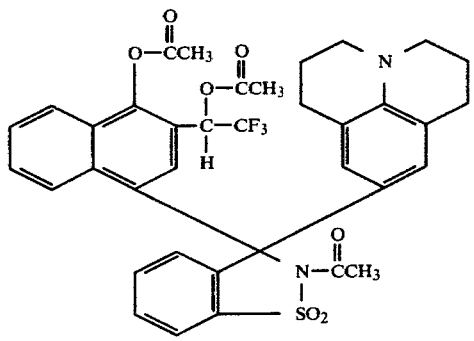

38. The compound

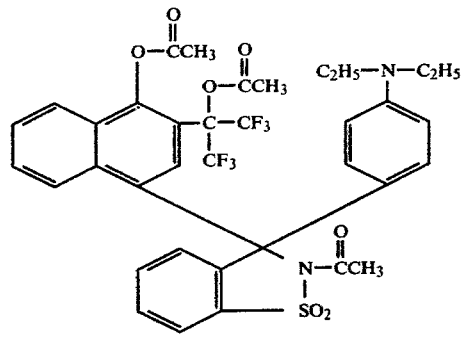

39. The compound

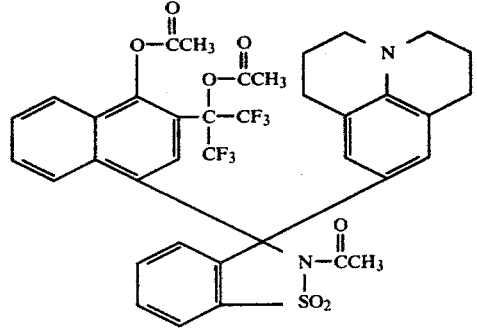

* * * * *